United States Patent [19]

Charlé et al.

[11] 3,978,204

[45] Aug. 31, 1976

[54] COSMETIC COMPOSITION CONTAINING MICROENCAPSULATED SOLVENTS FOR NAIL ENAMEL

[75] Inventors: Roger Charlé, Soisy-sous-Montmorency; Charles Zviak, Franconville; Gregoire Kalopissis, Paris, all of France

[73] Assignee: L'Oreal, Paris, France

[22] Filed: Dec. 12, 1974

[21] Appl. No.: 532,293

Related U.S. Application Data

[62] Division of Ser. No. 247,583, April 26, 1972, abandoned, which is a division of Ser. No. 8,719, Feb. 4, 1970, Pat. No. 3,691,270.

[30] Foreign Application Priority Data

Feb. 4, 1969 Luxemburg.............................. 57905

[52] U.S. Cl................................ 424/28; 15/104.93; 132/88.7; 162/158
[51] Int. Cl.$^2$..................... A61K 9/70; A45D 40/26; B08B 1/00
[58] Field of Search..................... 424/28; 15/104.93; 117/36.2, 36.9, 100; 128/268; 132/88.7; 162/127, 175, 158; 252/316

[56] References Cited
UNITED STATES PATENTS

| | | | |
|---|---|---|---|
| 2,949,403 | 8/1960 | Andreadis et al..................... | 424/60 |
| 3,137,631 | 6/1964 | Soloway........................... | 252/316 X |
| 3,196,478 | 7/1965 | Baymiller et al.................... | 401/132 |
| 3,334,374 | 8/1967 | Watkins............................. | 401/196 |
| 3,334,790 | 8/1967 | Eaton................................ | 222/107 |
| 3,384,536 | 5/1968 | Sandberg et al.................... | 162/175 |
| 3,441,353 | 4/1969 | Clapp................................ | 401/132 |
| 3,464,413 | 9/1969 | Goldfarb et al..................... | 128/268 |
| 3,472,675 | 10/1969 | Gordon et al...................... | 117/36.9 |
| 3,516,846 | 6/1970 | Matson............................. | 117/36.2 |
| 3,565,753 | 2/1971 | Yurkowitz......................... | 162/127 |
| 3,619,842 | 11/1971 | Maierson.......................... | 15/104.93 |

*Primary Examiner*—Shep K. Rose
*Attorney, Agent, or Firm*—Cushman, Darby & Cushman

[57] ABSTRACT

A process for preparing a cosmetic blotting paper toweling composition for the skin consisting essentially of a flexible solid blotting paper toweling support having a multiplicity of mechanical pressure rupturable, cosmetic containing microcapsules, which are homogeneously distributed therein, comprises dispersing the microcapsules in a liquid blotting paper paste phase at a time when the liquid blotting paper paste phase has a density close to that of the microcapsules so that the microcapsules are homogeneously distributed therein and solidifying the liquid phase to produce said cosmetic composition.

5 Claims, No Drawings

COSMETIC COMPOSITION CONTAINING MICROENCAPSULATED SOLVENTS FOR NAIL ENAMEL

This is a division of application Ser. No. 247,583 filed Apr. 26, 1972 now abandoned which is a division of Ser. No. 8,719, filed Feb. 4, 1970 now U.S. Pat. No. 3,691,270.

The present invention relates to a cosmetic make-up removing or treating composition, characterized essentially in that it is incorporated in a flexible support and that the activity of the cosmetic agent that is utilized cannot be effected until sufficient mechanical pressure has been exerted upon the said support at the moment of its application.

Cosmetic makeup removing or treating towels are available, for example, in the form of a "blotting paper" type paper which has on its surface or in the body a known cleansing product. The disadvantage of such paper is that the product on storage can be altered or can spot adjacent objects.

The present invention is intended to obviate the above mentioned disadvantages and to impart to the makeup removing or treating cosmetic towel practically indefinite storage.

The present invention thus has as its subject a cosmetic makeup removing or treating composition which softens or moisturizes the skin, protecting it from the sun's rays, or acts as a wrinkle-preventive.

The present invention also relates to the process for the preparation of towels and "cotton" as cited above.

The term "cotton" as used here means a cosmetic support which is presented as a bulk and not as a surface, the material which constitutes the said cotton being extremely diverse.

According to the invention, it has been found possible to prepare makeup removing or treating towels and cotton without the above indicated drawbacks by microencapsulation of the cosmetic agents and distribution thereof inside the support or even simply adhered to the support surface.

The process of microencapsulation of the active cosmetic agents does not in itself constitute part of the present invention when the microencapsulation of the said agents is effected separately and the microcapsules are then used as starting materials.

In accordance with the present invention the above described cosmetic towels and cottons are prepared by a process characterized in that the microcapsules containing the cosmetic agent are introduced in the course of the preparation of the solid cosmetic support itself and that there is then directly effected the workup of the preparations thus obtained, the microcapsules remaining unaltered in the course of this treatment.

According to a first method of preparation, the starting product is a "blotting paper" paste, and there is incorporated in the said paste the microcapsules here designated as C, which were prepared beforehand. The preparation of cosmetic towels or cottons is then effected similarly to the prepartion of ordinary blotting paper, operating however in conditions which are compatible on the one hand with the cosmetic agent contained in microcapsules C and on the other hand with the compounds that constitute their envelope, here designated E.

Compounds are therefore selected for envelopes E which have good mechanical resistance to heat and a sufficient degree of elasticity.

According to a modification of the process of the present invention, instead of blotting paper there is used as support a synthetic polymer or copolymer which is thermosetting or obtained by polycondensation or catalytic polyaddition. In any case, it is necessary to satisfy the following conditions in the course of their manufacture:

the monomers or prepolymers or the base products of polyaddition or polycondensation which are used as starting material must be sufficiently fluid to allow ready introduction of microcapsules C and the good homogenization thereof, the respective densities of capsules C and of the liquid phase possibly being adjusted; the compounds of the constituents that form envelopes E must have good heat resistance and sufficient elasticity;

envelopes E must chemically resist the action of the above mentioned liquid phase.

The final preparation of the synthetic product containing the microcapsules is effected by a thermal or catalytic treatment in which the above conditions are observed, to obtain preferably, depending upon the polymer compound that is used, either films or foils that are quite thin, or a porous material with all desired degrees of density and containing the cosmetic microcapsules included in the body of the polymer.

The interest of cosmetic cottons thus prepared and in the form of a thin foamed material is evident, the microencapsulated makeup remover or treating product then appearing after pressure of the fingers or pressure attained by application on the desired spot. A thin cosmetic towel can also be made from the same material.

The films in which microcapsules containing makeup remover and/or cosmetic treating agents are advantageously used in blotting paper type towels which form pockets in which they are introduced as a single cutout having the form of the pocket, or as a plurality of preferably lamellar cutouts. Thus polyvalent towels can be prepared, with different colors corresponding to the respective locations of the microcapsule sheets which have different properties.

According to another modification, the cosmetic towel of the invention has one surface for makeup removal and one treating surface. In this case, the blotting paper type towel presents two separate pockets, separated by a tight film, the two sides receiving respectively the makeup remover sheet and the treating sheet.

As compounds utilized for preparation of envelope E of the microcapsules which answer to the conditions indicated above, there are preferably used the following resins: polyamides, chlorated polyethers, epoxy resins, polysulfones, formaldehyde urea, polyurethane, aromatic polyimides, mixed cellulose esters or starch with dicarboxylic acids such as phthalic acid, succinic acid, maleic acid, polyvinyl pyridines, polyvinyl quinoleines, polyvinyl imidazoles, polyethylene, polypropylene, gelatin treated with formol or with gum arabic. Many other types of resins can likewise be used, but among the mentioned resins the polyamides, chlorated polyethers, epoxy resins and polyalkylenes are most used.

The compounds used for preparation of the synthetic resin films which contain microcapsules C are preferably selected from among the following: acetal homopolymers and copolymers, methyl polymethacrylate as well as copolymers thereof formed with styrene and alphamethyl styrene, ethyl cellulose, cellulose acetate, cellulose propionate, cellulose acetobutyrate, vinyl polymers and copolymers such as vinylidene chloride or polyvinyl dichloride, polystyrenes and copolymers of styrene-acrylonitrile, allyl resins, casein base resins, polyethylene, melamine formaldehyde resin, phenol formaldehyde resins etc.

The compounds for formation of a porous support are selected from among the following: polyurethane, cellulose acetate, formaldehyde urea, polystrene, styrene-acrylonitrile, polyvinyl chloride, polyethylene, epoxy resins etc.

Preferably densities of 0.01 to 0.60 and preferably 0.05 to 0.25 are used for the closed-cell or open-cell alveolar support prepared with these resins.

An essential characteristic of the process of the invention resides in the appropriate choice of support materials and of the compound which forms envelopes E of capsules C so that the latter withstand the conditions of manufacture, especially the thermal conditions, the active agent that they contain being however readily released by mechanical pressure at the moment of use.

Microcapsules C contain either makeup remover, or skin-treating products as milk, oils, creams, emulsions, or they may contain makeup foundation or cosmetic products in general for local application such as gradual dyeing of the hair.

The maufacture of the towels and cosmetic cottons is accomplished as follows:

The suspension or mixture of the initial liquid compounds that are to constitute the support of capsules C in the final product is prepared.

The said support is prepared, i.e. either blotting paper from paper paste or synthetic polymer from the monomer or liquid prepolymer which is thermosetting, or catalytically condensable products, the latter possibly yielding foams, and microcapsules C which have been prepared separately are introduced at an appropriate moment in this process, conditions particularly of temperature and pressure being appropriately adjusted.

Microcapsules C are introduced either directly into the mass at a moment in which its fluidity is still sufficient, the density of the microcapsules moreover being close to that of the liquid phase, or they are introduced by spraying when it is desired to incorporate them in a thin foil, before termination of the polymerization of the said foil.

At the end of the manufacturing process, there are thus obtained microcapsules C incorporated in the body of the support, the said support being a blotting paper, a thin film, or a porous mass of suitable synthetic material.

Workup or necessary cutting is then effected, to prepare towels or cosmetic cottons of the invention.

In general, when the microcapsules are introduced in the course of manufacture of the cosmetic support which is in the form of a liquid or a suspension, the best possible homogenization is obtained by suitable mixing by agitation, shaking or blowing in of a gas. The density of the liquid or of the suspension is then adjusted to that of the microcapsules by addition of one of the components of the support or an appropriate inert substance, and premixtures can be prepared which contain the microcapsules with a fraction of the support or some of its components. It is also possible to select microcapsules whose density corresponds to that of the liquid or of the suspension at the moment of their introduction.

Besides, the microcapsule envelopes are selected readily to resist slight pressure as well as temperatures of the order of 50° to 60°C and in certain instances temperatures distinctly higher when such temperatures are required by the process for preparation of the support.

The following non-limiting examples in which parts and percentages refer to weight are given by way of illustration and allow a fuller understanding of the present invention.

EXAMPLE 1

Towel containing a microencapsulated makeup remover milk:

The following makeup remover composition is prepared:

| | |
|---|---|
| "O.E." stearyl alcohol (oxyethylene) | 4.0 |
| ropy vaseline | 6.0 |
| isopropyl myristate | 5.0 |
| glycerol | 10.0 |
| antiferment | 0.1 |
| perfume | 0.3 |
| water to make up | 100.0 |

The makeup remover milk is then microencapsulated by the known technique, using polypropylene, the microcapsules having an average dimension of 50 to 100 microns and preferably from 60 to 80. The said microcapsules are dispersed in a blotting paper paste at the moment at which the density of the said paste is such that the microcapsules are distributed in it with sufficient uniformity. The said blotting paper is allowed to drain and it is dried on a form in thin layers, possibly with slight pressure, or the microcapsules are "flash" projected onto the surface of sheets of blotting paper preliminarily coated with an adhesive layer. The sheets are cut to the desired size and thus makeup remover towels ready for use are obtained. The microcapsules release the makeup remover milk by simple pressure that crushes the microcapsules.

EXAMPLE 2

Towel containing sun oil in microcapsules. The following oily solution is prepared:

| | |
|---|---|
| almond oil | 93.99 |
| cholesterol | 0.50 |
| rancidity preventer | 0.01 |
| benzyl salicylate | 5.00 |
| perfume | 0.50 |

This oil, which constitutes an excellent filter for solar radiation, is used in the microencapsulated state, said encapsulation being effected by a known process using ethyl cellulose or polyvinyl acetal, the microcapsules having a size between 50 and 100 microns, preferably 60 to 100 microns.

On cotton fabric cut to the desired shape and preliminarily coated with an adhesive layer, the microcapsules are dispersed either by a suitable mechanical device or by projection using compressed air or gas.

A support ready for use is thus obtained. The microcapsules release the sun-protection oil that they contain by simple pressure against the skin.

The produce is thus made up in a way that is both light and easy to use.

EXAMPLE 3

Films cut in thin sheets containing a microencapsulated cream incorporated in cosmetic towels, possibly with a plurality of separations.

A cream is prepared which contains:

| | |
|---|---|
| tragacanth gum | 2.0 |
| extra fine kaolin | 30.0 |
| titanium dioxide | 3.0 |
| cerebromedullary extract | 4.0 |
| stabilizer | 0.3 |
| physiological serum | 10.0 |
| perfume | 0.2 |
| water to make up | 100.0 |

This microencapsulated cream is prepared by the known process, using sytrene copolymers and vinyl ester or vinyl ether, or polymers soluble at an alkaline pH and insoluble at an acid pH, like acrylic acid polymers.

Microcapsules 1 to 100 microns in size are obtained, preferably 20 to 50 microns.

A liquid film is also prepared which has a thickness of 30 to 40 microns, constituted by cellulose acetobutyrate in a solvent, and the above described microcapsules are sprayed onto this film, the said microcapsules containing the above described treating prepartion comprising a softening cream.

According to a modification, the cellulose acetobutyrate and microcapsule mixture is prepared and homogenized and spread in thin films.

After evaporation of the solvent, a thin film is obtained which contains the microcapsules and this film cut into sheets or in layers of desired size and shape are incorporated into blotting paper towels which form a pocket that may present separations.

EXAMPLE 4

Cosmetic cotton or towel of porous material containing microencapsulated makeup base.

A makeup foundation of the following composition is prepared:

| | |
|---|---|
| styrene | 5.0 |
| isopropyl myristate | 6.0 |
| vaseline oil | 20.0 |
| glycerol stearate | 3.0 |
| propylene glycol | 2.0 |
| triethanolamine | 2.0 |
| preservative | 0.2 |
| titanium dioxide | 10.0 |
| carboxymethyl cellulose | 1.5 |
| yellow iron oxide | 2.0 |
| red iron oxide | 1.0 |
| carbon black | 0.3 |
| demineralized water to make up | 100.0 |

This cream is microencapsulated by known processes using propylene or polyethylene, the size of the microcapsules being 1 to 100, preferably 30 to 40 microns.

Upon preparation of an alveolar polyurethane resin, before blowing in of carbon dioxide, the above microcapsules containing the makeup foundation cream are introduced.

After having effected a perfect distribution of the microcapsules in the resin, preparation of the alveolar polymer is continued, conditions of temperature and pressure, as well as the characteristics of the microcapsules being respectively and reciprocally appropriate.

Workup and cutting into cosmetic towels or cottons is then effected.

When they are used, these preparations release a makeup foundation, by pressure and crusing of the microcapsules, the said foundation spreading on the skin as the user requires.

Or again, as in the preceding example, it is possible to project the makeup foundation microcapsules onto the surface of a cut support which has the selected thickness and configuration.

EXAMPLE 5

A flexible cosmetic towel containing a microencapsulated dye of the following composition is prepared:

| | |
|---|---|
| oxyethylene lauryl alcohol | 5.0 |
| substituted fatty amine | 5.0 |
| copra amide | 4.0 |
| substituted aminophenol | 2.0 |
| substituted diaminobenzene | 2.0 |
| aqueous solution containing 20% ammonia | 1.5 |
| perfume | 0.1 |
| water to make up | 100.0 |

This dye composition is used in microcapsules prepared by a known process, using casein or an epoxy resin, the microcapsules being 20 to 100 microns, preferably 40 to 60 microns in size.

These microcapsules are placed or projected onto a flexible support which may be paper, cotton fabric or a film of suitable plastic material, the above mentioned supports being preliminarily coated with a suitable adhesive substance. There is thus obtained a composition which is simple and practical in form, allowing local application of a dye product whose shade develops by oxidation in air.

We claim:

1. A process for the preparation of a cosmetic blotting paper toweling composition consisting essentially of a flexible solid blotting paper toweling support having a multiplicity of microcapsules, encapsulating said cosmetic, homogeneously distributed therein, said flexible solid blotting paper toweling support being adapted when cut to towels to be applied topically to the skin and said microcapsules having average dimensions of 50 to 100 microns and being rupturable by mechanical pressure to release said cosmetic, the walls of said microcapsules being inert to said cosmetic, the steps comprising dispersing said microcapsules in a liquid blotting paper paste phase which on solidification by draining and drying yields said flexible blotting paper toweling support, said microcapsules being dispersed therein at a time when said liquid blotting paper paste phase has a density close to that of said microcapsules so that said microcapsules are homogeneously distributed therein and solidifying by draining and drying said liquid blotting paper paste phase having said microcapsules homogeneously distributed therein to produce said cosmetic composition.

2. The process of claim 1 which includes adjusting the density of said liquid blotting paper paste phase so that it is close to the density of said microcapsules.

3. The process of claim 1 wherein said cosmetic is a makeup remover composition.

4. A process for the preparation of a cosmetic blotting paper towel composition consisting essentially of a flexible solid blotting paper towel support having a multiplicity of microcapsules having average dimensions of 50 to 100 microns and encapsulating a makeup remover composition, said microcapsules being homogeneously distributed in said flexible solid blotting paper towel support adaptable to be applied topically to the skin, the steps comprising dispersing said microcapsules in a blotting paper paste at a time when the density of said paste is close to that of said microcapsules so that said microcapsules are homogeneously distributed therein, draining and drying said blotting paper paste having said microcapsules homogeneously distributed therein on a form in a thin layer and cutting said layer to provide makeup remover blotting paper towels wherein said microcapsules release the makeup remover composition by simple pressure that crushes the microcapsules.

5. The process of claim 4 wherein the microcapsules are made of polypropylene.

* * * * *